A61F 9/06
2/427

(12) United States Patent
Welsh

(10) Patent No.: US 12,329,228 B2
(45) Date of Patent: Jun. 17, 2025

(54) REPLACEMENT STRAP FOR HELMET SUSPENSION

(71) Applicant: Welshco LLC, Lawton, OK (US)

(72) Inventor: Geoffrey Welsh, Lawton, OK (US)

(73) Assignee: Welshco LLC, Lawton, OK (US)

( * ) Notice: Subject to any disclaimer, the term of this patent is extended or adjusted under 35 U.S.C. 154(b) by 71 days.

(21) Appl. No.: 18/102,194

(22) Filed: Jan. 27, 2023

(65) Prior Publication Data

US 2023/0240406 A1 Aug. 3, 2023

Related U.S. Application Data

(60) Provisional application No. 63/304,752, filed on Jan. 31, 2022.

(51) Int. Cl.
*A42B 3/08* (2006.01)
*A42B 3/14* (2006.01)
*A61F 9/06* (2006.01)

(52) U.S. Cl.
CPC .............. *A42B 3/08* (2013.01); *A42B 3/145* (2013.01); *A61F 9/06* (2013.01)

(58) Field of Classification Search
CPC A61F 9/06; A42B 3/145; A42B 3/147; A42B 3/085
USPC ............................................................ 2/8.2
See application file for complete search history.

(56) References Cited

U.S. PATENT DOCUMENTS

| 1,750,036 | A | * | 3/1930 | Chambers | ................. | A61F 9/06 |
| | | | | | | 2/427 |
| 1,885,426 | A | * | 11/1932 | Flood | ......................... | A61F 9/06 |
| | | | | | | 2/8.2 |
| 2,016,775 | A | | 10/1935 | Gingg | | |
| 2,135,397 | A | | 11/1938 | Jackson | | |
| 2,194,492 | A | * | 3/1940 | Bowers | ..................... | A61F 9/06 |
| | | | | | | 2/8.1 |
| 2,390,006 | A | * | 11/1945 | Severy | ...................... | A61F 9/06 |
| | | | | | | 2/8.1 |
| 2,469,810 | A | * | 5/1949 | Bowers | ..................... | A61F 9/06 |
| | | | | | | 2/8.1 |
| 2,487,848 | A | * | 11/1949 | Bowers | ..................... | A61F 9/06 |
| | | | | | | 2/8.1 |
| 2,915,756 | A | * | 12/1959 | Rex | ........................ | A61F 9/06 |
| | | | | | | 2/8.1 |

(Continued)

FOREIGN PATENT DOCUMENTS

CN 109512575 A 3/2019
CN 209645217 U 11/2019
(Continued)

*Primary Examiner* — Grace Huang
(74) *Attorney, Agent, or Firm* — Silverline Legal, PLLC; Tynia A. McQuigg; Drew T. Palmer

(57) ABSTRACT

A replacement rear strap assembly is provided for use on a helmet that has a headgear assembly. The headgear assembly has a front strap, a top strap, a pair of hubs between the front strap and top strap, and a pair of connection bosses extending from the pair of hubs. The replacement rear strap assembly includes a pair of adapter rings and a replacement strap extending between the pair of adapter rings. In some embodiments, each of the pair of adapter rings includes an adapter ring aperture. In some embodiments, each of the adapter ring apertures is sized and configured to be placed over a corresponding one of the pair of connection bosses.

2 Claims, 6 Drawing Sheets

(56) References Cited

U.S. PATENT DOCUMENTS

| | | | |
|---|---|---|---|
| 3,075,201 A | | 1/1963 | Lindblom |
| 3,696,442 A * | 10/1972 | Amundsen | A61F 9/06 2/8.1 |
| 4,040,123 A * | 8/1977 | Williams | A61F 9/06 2/10 |
| 5,381,560 A * | 1/1995 | Halstead | A42B 3/085 2/421 |
| 6,694,530 B2 * | 2/2004 | Maloney | A42B 3/185 2/10 |
| 7,865,968 B2 * | 1/2011 | Lilenthal | A42B 3/225 2/8.2 |
| 7,870,617 B2 * | 1/2011 | Butler | A42B 3/145 2/410 |
| 7,975,318 B2 * | 7/2011 | Zuber | A42B 3/145 2/410 |
| 8,850,624 B2 * | 10/2014 | Gleason | A42B 3/085 2/181 |
| 8,990,963 B2 * | 3/2015 | Matthews | A61F 9/022 2/8.2 |
| 9,737,107 B2 * | 8/2017 | Xiong | A42B 3/142 |
| 10,357,401 B2 * | 7/2019 | Hsu | A61F 9/06 |
| 10,441,019 B2 * | 10/2019 | Huh | A42B 3/12 |
| 11,969,043 B2 * | 4/2024 | Brose | A42B 3/14 |
| 2012/0054936 A1 * | 3/2012 | Cornell | A42B 3/227 2/9 |
| 2012/0311752 A1 * | 12/2012 | Ahlgren | A61F 9/06 2/416 |
| 2013/0047312 A1 * | 2/2013 | Wilson | A41D 13/0012 2/69 |
| 2014/0259252 A1 * | 9/2014 | Seo | A61F 9/022 2/8.2 |
| 2020/0397615 A1 | 12/2020 | Williams | |

FOREIGN PATENT DOCUMENTS

| | | | |
|---|---|---|---|
| CN | 212592704 U | 2/2021 | |
| DE | 102004005757 A1 * | 8/2005 | A42B 3/185 |

\* cited by examiner

REPLACEMENT STRAP FOR HELMET SUSPENSION

CROSS REFERENCE TO RELATED APPLICATIONS

This application claims the benefit of U.S. Provisional Patent Application No. 63/304,752 filed Jan. 31, 2021, and incorporates said provisional application by reference into this document as if fully set out at this point.

FIELD OF THE INVENTION

This invention relates generally to the field of protective helmets and more particularly, but not by way of limitation, to a replacement strap system for a helmet suspension.

BACKGROUND

A wide variety of helmets are used for safety purposes in industrial and recreational activities. Hard hats and welding helmets are commonly worn to protect workers from impact, sparks, and other workplace hazards. For example, FIG. 1 depicts a PRIOR ART welding helmet 200. The welding helmet 200 includes a face shield 202, a lens 204, and a standard headgear assembly 206. The face shield 202 protects the welder's face from sparks, slag and debris produced during the welding process. The lens 204 is permanently or temporarily tinted to reduce the high intensity light from harming the welder's eyes. The standard headgear assembly 206 supports the helmet 200 on the head of the welder. In some cases, the standard headgear assembly 206 is referred to as a helmet "suspension" because the helmet 200 rides on the standard headgear assembly 206, which is in turn connected to the welder's head.

The PRIOR ART standard headgear assembly 206 is depicted in isolation in FIGS. 2 and 3. The standard headgear assembly 206 generally includes a front strap 208, a standard rear strap 210, a top strap 212, and two hubs 214. In the embodiment depicted in FIGS. 1-3, the front strap 208, standard rear strap 210 and top strap 212 each extend between and are joined together at the two hubs 214.

The front strap 208 may optionally include a cloth sweatband 216 designed to absorb perspiration from the welder's forehead. The standard rear strap 210 includes a rear strap adjustment mechanism 218 that is configured to increase or decrease the length of the standard rear strap 210, which enables the standard headgear assembly 206 to be tightened around the back of the welder's head. The internal circumference created by the front strap 208, the standard rear strap 210 and the connecting hubs 214 can be adjusted to match the circumference of the welder's head. In the embodiment depicted in FIGS. 1-3, the rear strap adjustment mechanism 218 includes a ratcheting system in which a dial is rotated to increase or decrease the length of the standard rear strap 210. For heavier helmets 200, it is particularly important for the standard rear strap 210 to be tightened about the welder's head so that the helmet 200 remains securely fastened during use.

The top strap 212 includes a top strap adjustment mechanism 220. In the embodiment depicted in FIGS. 1-3, the top strap adjustment mechanism 220 includes a series of adjustment holes and posts that cooperate to adjust the length of the top strap 212. In this way, the length of the top strap 212 can be adjusted so that the front strap 208 and standard rear strap 210 are correctly positioned on the welder's head.

The face shield 202 is connected to the standard headgear assembly 206 with fasteners 222. Each fastener 222 includes a threaded bolt 224 with a bolt base 226 and a nut 228 that is configured to be hand-tightened onto the threaded bolt 224. The hubs 214 each include an attachment boss 230 that is designed to contact the inside of the sides of the face shield 202. Each attachment boss includes a fastener bore 232, which is configured to receive the threaded bolt 224. The bolt base 226 is preferably larger than the fastener bore 232. Each attachment boss 230 also has an outer perimeter defined by side surfaces 234.

As best shown in FIGS. 2-3, the attachment bosses 230 extend outward from the hubs 214 such that the bolt base 226 is retained within the interior of the corresponding attachment boss 230 and not in contact with the welder's head. Each of the threaded bolts 224 extends through the corresponding fastener bore 232 and through a mating hole in the face shield 202, where the nut 228 is secured to the threaded bolt 224 on the outside of the face shield 202. Tightening the nut 228 onto the threaded bolt 224 applies a compressive force between the attachment boss 230 and face shield 202.

In most helmets 200, the front strap 208, standard rear strap 210 and top strap 212 are manufactured from a thermoplastic through an injection molding process. In this way, the front strap 208, standard rear strap 210, top strap 212, hubs 214 and attachment bosses 230 can be constructed as a unitary piece that is assembled by connecting two ends of the standard rear strap 210 at the rear strap adjustment mechanism 218 (which may be separately manufactured) and connecting two ends of the top strap 212 at the top strap adjustment mechanism 220.

Many helmets 200 are designed such that the face shield 202 can be pivoted from a deployed (lowered) position to protect the welder's face while welding to a retracted (raised) position that permits the welder to see under the raised helmet while preparing for a welding operation. To support the weight of the face shield 202 in the raised position, the nuts 228 must be sufficiently tightened to apply an appropriate amount of compression and friction between attachment bosses 230 and the inside of the face shield 202.

Although the basic form and function of the standard headgear assembly 206 depicted in FIGS. 1 and 2 has found widespread acceptance, the standard headgear assembly 206 nonetheless suffers from several deficiencies. In particular, the rear strap adjustment mechanism 218 is prone to failure after extended use. Because the rear strap adjustment mechanism 218 is tightened or loosened each time the helmet 200 is donned or doffed by the welder, the rear strap adjustment mechanism 218 often fails before the balance of the components within the helmet 200. In some cases, the standard rear strap 210 is uncomfortable, particularly when worn for extended periods. There is, therefore, a need for an improved headgear assembly for use in a hardhat, welding helmet or other helmet that includes a helmet suspension.

SUMMARY OF THE INVENTION

In one aspect, embodiments of the present disclosure are directed to a replacement rear strap assembly for use on a helmet, where the helmet has a headgear assembly that has a front strap, a top strap, a pair of hubs between the front strap and top strap, and a pair of connection bosses extending from the pair of hubs. The replacement rear strap assembly includes a pair of adapter rings and a replacement strap extending between the pair of adapter rings. In some embodiments, each of the pair of adapter rings includes an adapter ring aperture. In some embodiments, each of the adapter ring apertures is sized and configured to be placed over a corresponding one of the pair of connection bosses. Each of the adapter ring apertures may be D-shaped. In several embodiments, the headgear assembly has a standard rear strap that extends between the pair of hubs. In other embodiments, the headgear assembly does not include a standard rear strap that extends between the paid of hubs.

In another aspect, embodiments of the present disclosure are directed to a method for adding a replacement rear strap assembly to a helmet that includes a standard headgear assembly that has a pair of hubs, a front strap extending between the pair of hubs, and a standard rear strap extending between the pair of hubs. The method includes the steps of removing the standard headgear assembly from the helmet, removing the standard rear strap from the standard headgear assembly to provide a modified headgear assembly, connecting the replacement rear strap assembly to the modified headgear assembly, and connecting the modified headgear assembly and replacement rear strap assembly to the helmet. In some embodiments, the standard headgear assembly further includes a pair of attachment bosses each extending from a corresponding one of the pair of hubs, and the step of connecting the replacement rear strap assembly includes the step of connecting an adapter ring of the replacement rear strap assembly over each of the pair of attachment bosses. The step of removing the standard rear strap from the standard headgear assembly may further include the step of severing the standard rear strap from the pair of hubs on the standard headgear assembly. In some embodiments, the step of connecting the modified headgear assembly and replacement rear strap assembly to the helmet includes the step of connecting the modified headgear assembly to the helmet with fasteners.

DETAILED DESCRIPTION

Figure 1:
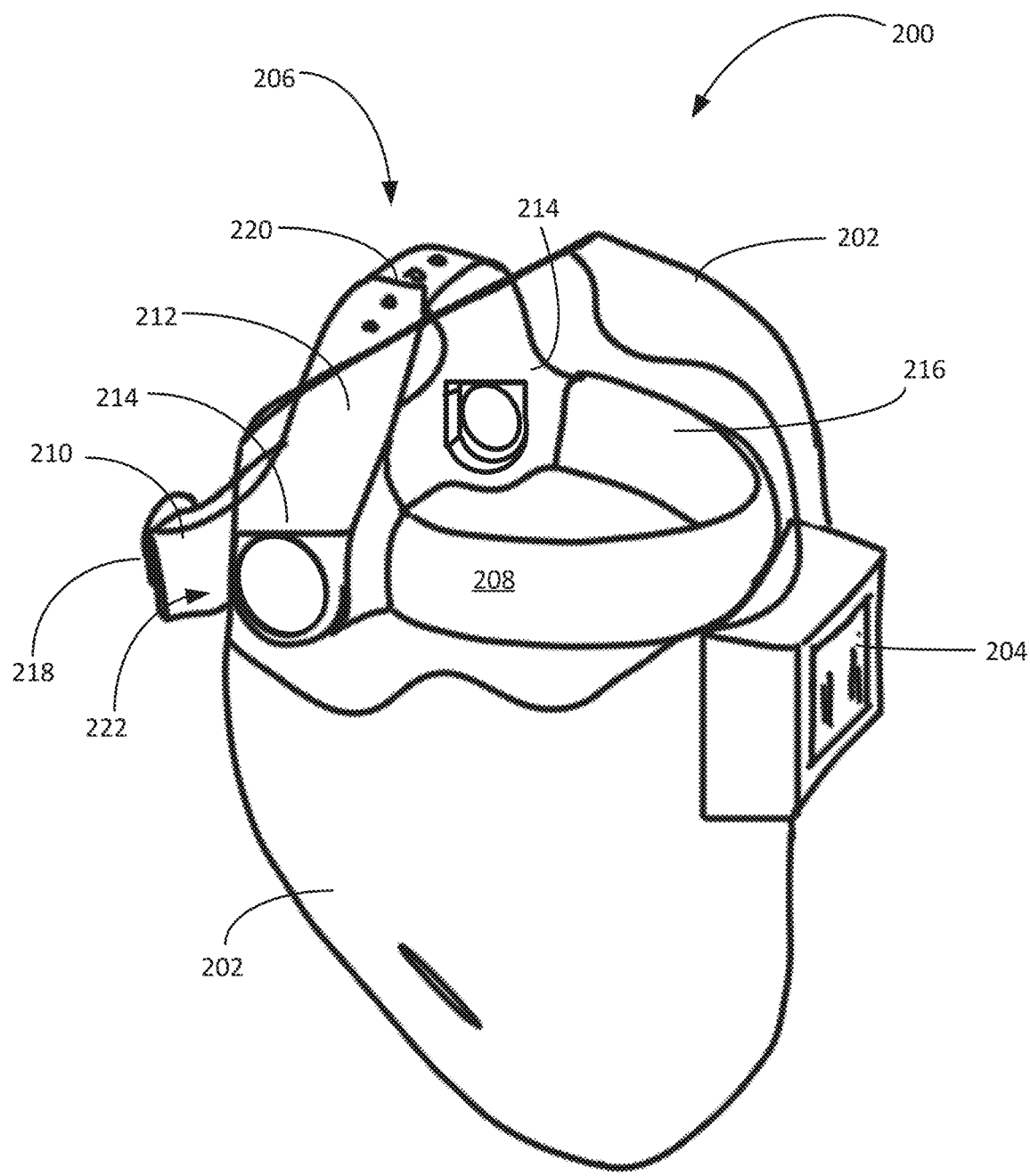
FIG. 1 provides a partial cutaway depiction of a PRIOR ART welding helmet with headgear assembly.
Figure 2:
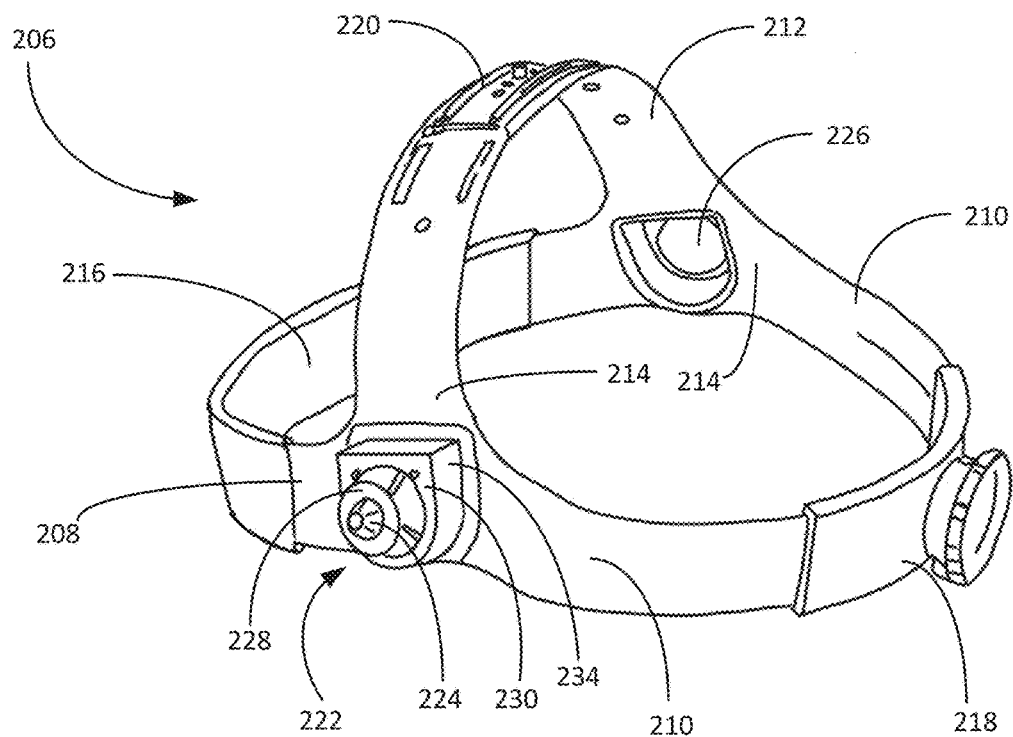
FIG. 2 is a perspective view of the PRIOR ART headgear assembly of FIG. 1.
Figure 3:
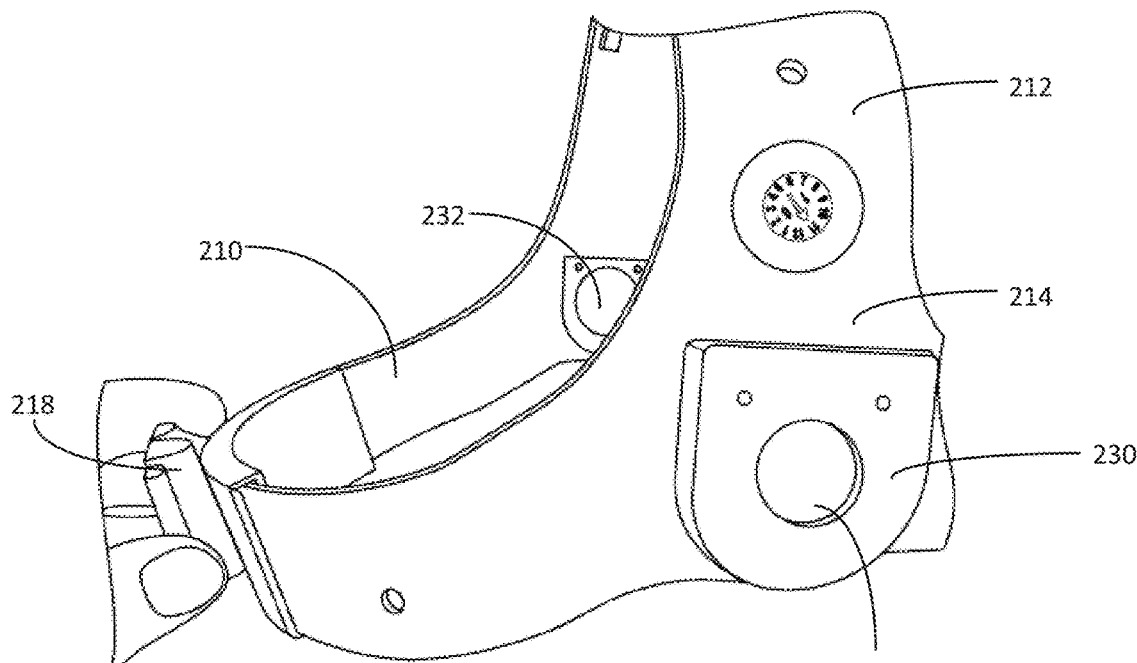
FIG. 3 is a close-up view of the rear strap and adjustment mechanism from the PRIOR ART headgear assembly of FIG. 2.
Figure 4:
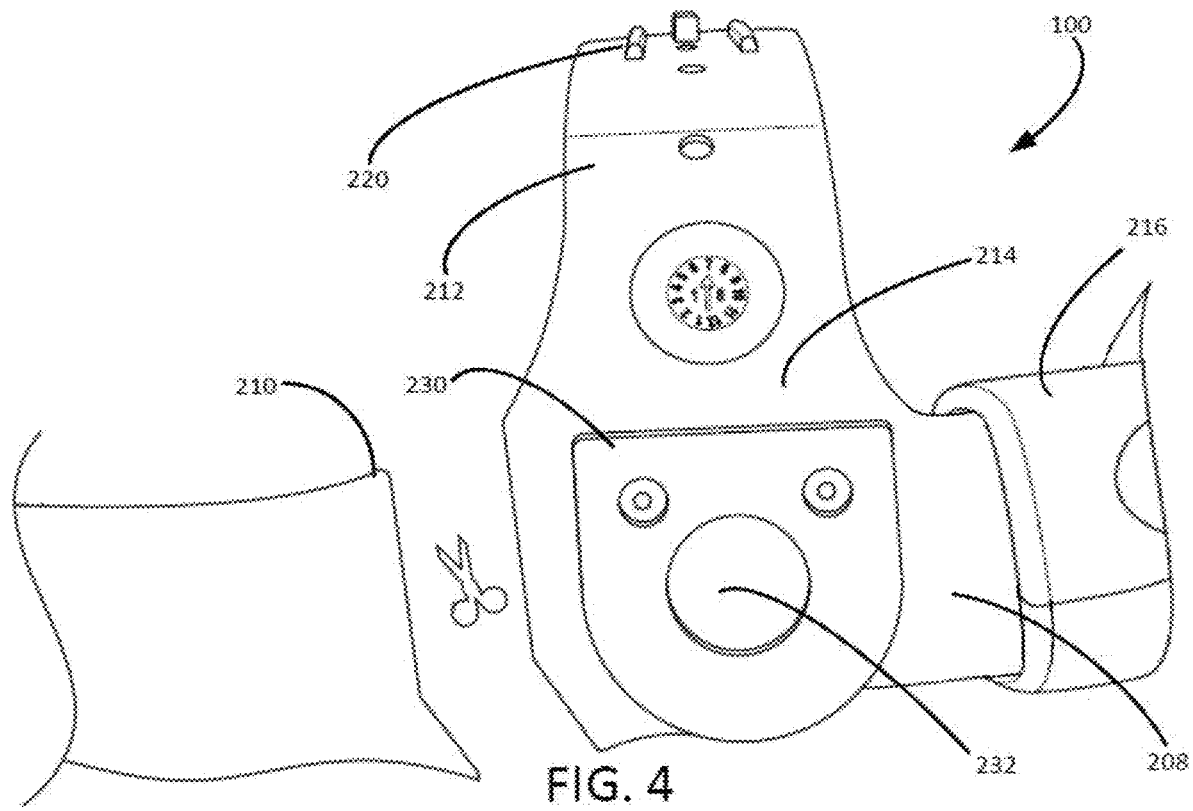
FIG. 4 depicts a portion of the headgear assembly modified in accordance with an exemplary embodiment of the present invention.

In accordance with an exemplary embodiment, FIG. 4 depicts a modified headgear assembly 100. The modified headgear assembly 100 includes the front strap 208, top strap 212, hubs 214 and attachment bosses 230 common to the prior art standard headgear assembly 206, but the standard rear strap 210 and rear strap adjustment mechanism 218 have been removed. In some embodiments, the standard rear strap 210 can be removed simply by severing the standard rear strap 210 from both hubs 214. Scissors, utility knives or other cutting tools can be used to remove the standard rear strap 210 from the hubs 214. In other embodiments, a standard headgear assembly 206 may be modified during initial manufacture to omit the standard rear strap 210.

Figure 5:
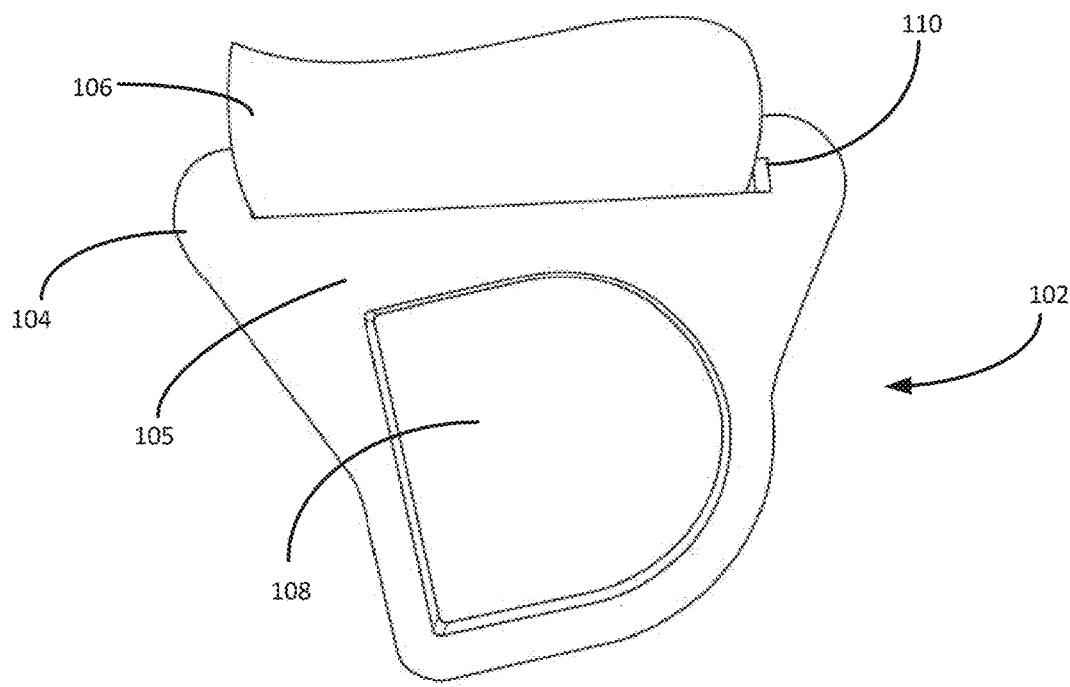
FIG. 5 depicts an adapter ring and replacement strap of the replacement strap assembly.
Figure 6:
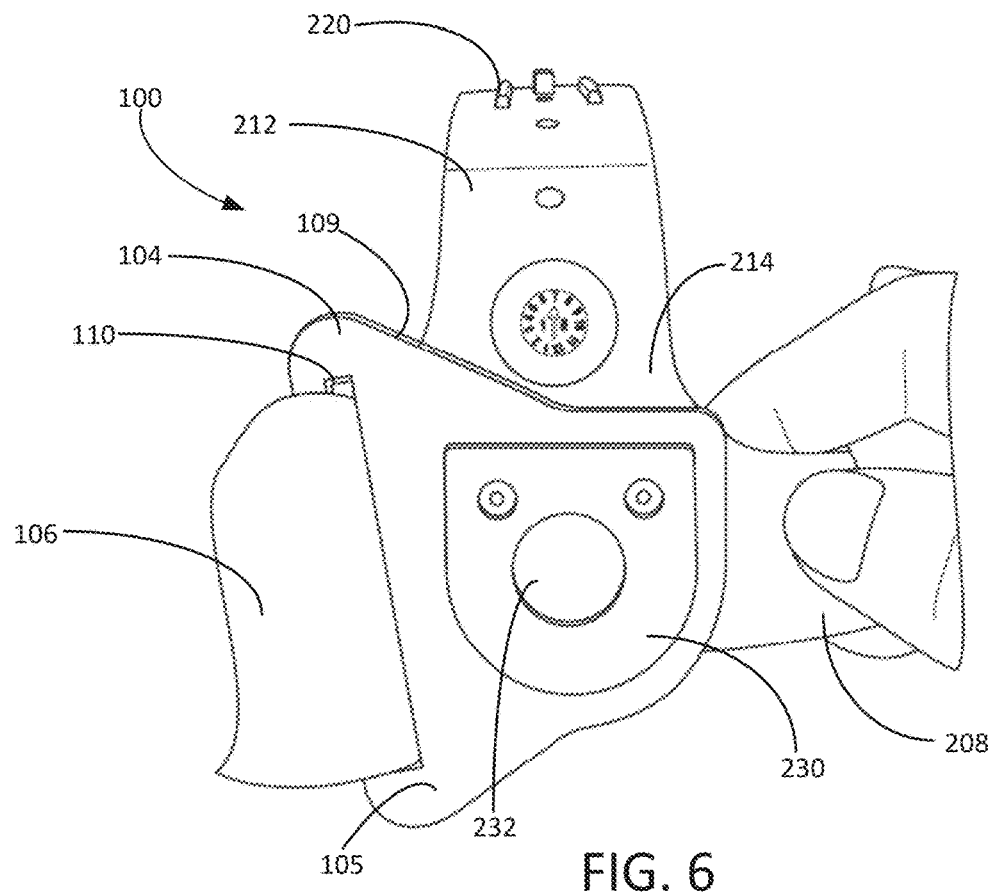
FIG. 6 depicts the replacement strap assembly of FIG. 5 connected to the modified headgear assembly of FIG. 4.
Figure 7:
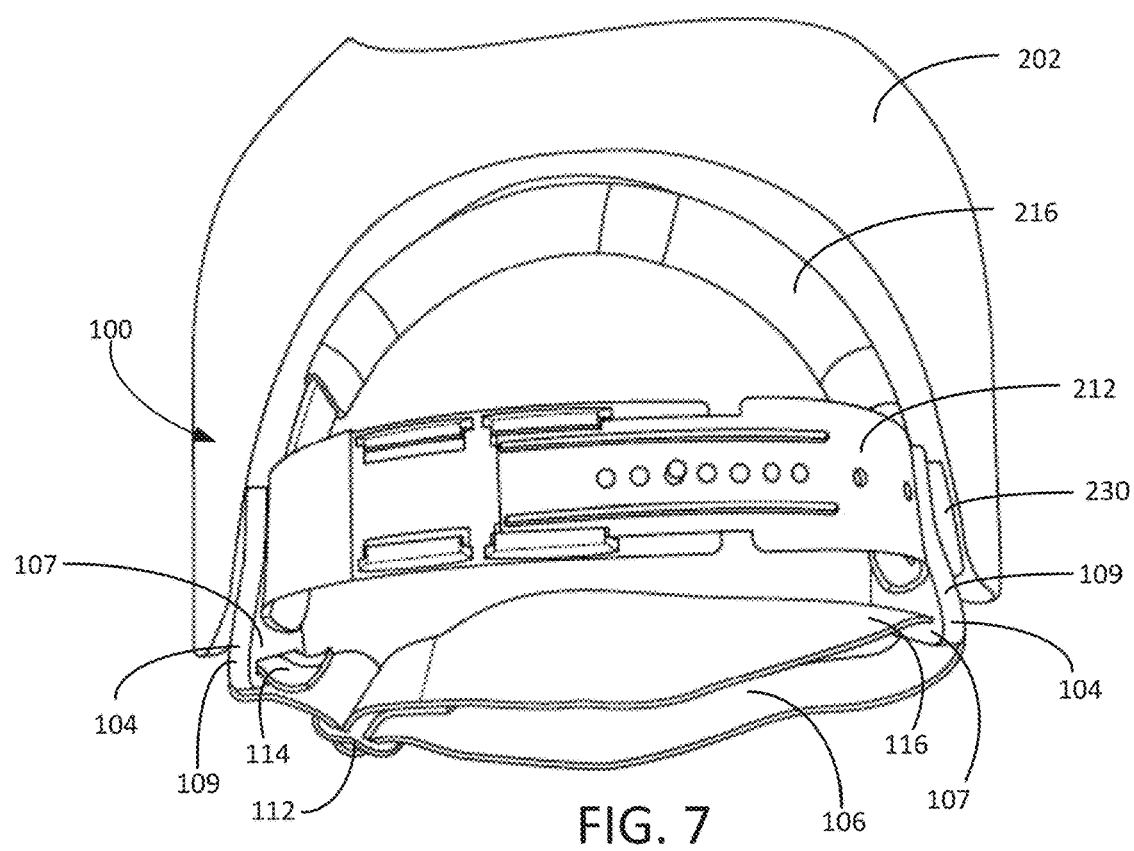
FIG. 7 provides a top view of the replacement strap assembly and modified headgear assembly within the helmet.

FIGS. 5-7 depict a replacement rear strap assembly 102. The replacement rear strap assembly 102 includes a pair of adapter rings 104 and a replacement strap 106 that extends between the pair of adapter rings 104. In some embodiments, a 3-D printing process is used to create each adapter ring 104 from any material suitable for a 3-D printer. In a preferred embodiment using a 3-D printing process, each adapter ring 104 is made from polycarbonate. It will be appreciated, however, that each adapter ring 104 may be made by any other suitable manufacturing processes and materials. Further, each adapter ring 104 may be made through the combination of one or more processes and from one or more materials. For example, each adapter ring 104 may be made from any suitable plastic, metal, wood, fabric or textile or any combination thereof.

Each adapter ring 104 includes an adapter ring aperture 108 that is designed to fit around a corresponding one of the attachment bosses 230. As illustrated in FIG. 4, the attachment boss 230 is "D-shaped" and as illustrated in FIG. 5, the adapter ring aperture 108 is congruently "D-shaped" and sized to closely fit over the attachment boss 230, such that the adapter ring aperture 108 corresponds to the outer perimeter of the attachment boss 230. It will be appreciated, however, that the adapter ring aperture 108 can be configured in any shape to match or accommodate the outer perimeter of a corresponding attachment boss 230, which may take on a variety of shapes and configurations.

Each adapter ring 104 further includes an upper surface 105, a lower surface 107 positioned opposite of the upper surface 105, and outer side surfaces 109 that extend from edges of the upper surface 105 to corresponding edges of the lower surface 107 and define an outer perimeter of the adapter ring 104. As shown in FIG. 11, the upper surface 105 may include a fillet 111 at its edges. In some embodiments, the fillet 111 is between 1 mm to 2 mm in width. In several embodiments, the fillet 111 is 1.2 mm in width. As illustrated in FIGS. 5-6 and FIGS. 10-11, the outer perimeter of each adapter ring 104 may be a streamlined shape with obtuse angles, curves, and straight edges.

Notwithstanding these exemplary embodiments, it will be appreciated that the outer perimeter of each adapter ring 104 can be configured in any shape or size to accommodate the adapter ring aperture 108. In some embodiments, the outer perimeter may include sharp angles rather than curves. As illustrated in FIG. 11, each adapter ring 104 may have a shape and size mirroring that of the other. However, it is appreciated that the adapter rings 104 in some embodiments can have a different shape and size from each other.

Each of the adapter rings 104 can include a strap slit 110 that is sized to permit the replacement strap 106 to be passed through the strap slit 110. In some embodiments, the strap slit 110 has a height that the same as the width of the replacement strap 106. In other embodiments, the strap slit 110 has a height that is greater than the width of the replacement strap 106. In a first preferred embodiment, the replacement strap 106 has a width of 2 inches. In a second preferred embodiment, the replacement strap 106 has a width of 1.5 inches. The replacement strap 106 of FIGS. 7 and 10 may be manufactured to any width and length that is suitable for securely fastening the modified headgear assembly 100 to a user's head during use. The replacement strap 106 has a short end 114 that passes through the strap slit 110 of a first adapter ring 104 and is then attached by stitching or by other suitable attachment devices, such as adhesive, snaps, buttons, clips or other closure mechanisms, to a first position on the replacement strap 106 that is proximate to the first adapter ring 104. The replacement strap 106 of FIGS. 7 and 10 also has a long end 116 that passes through the strap slit 110 of a second adapter ring 104 and is then attached by stitching or by other suitable attachment devices to a second position on the replacement strap 106 that is distant from the second adapter ring 104.

Figure 10:
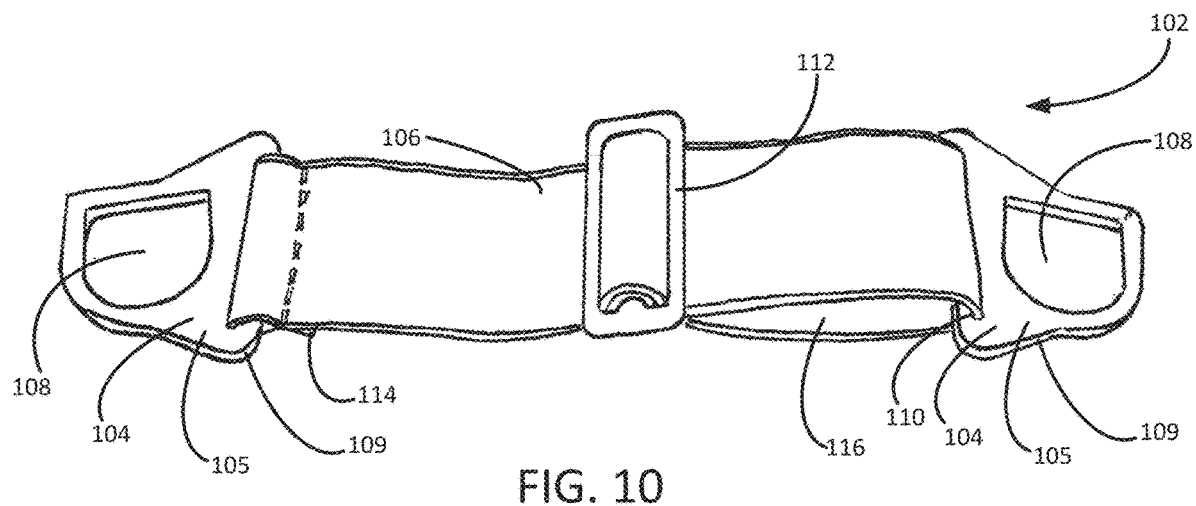
FIG. 10 depicts a rear view of the replacement strap assembly in accordance with an exemplary embodiment of the present invention.
Figure 11:
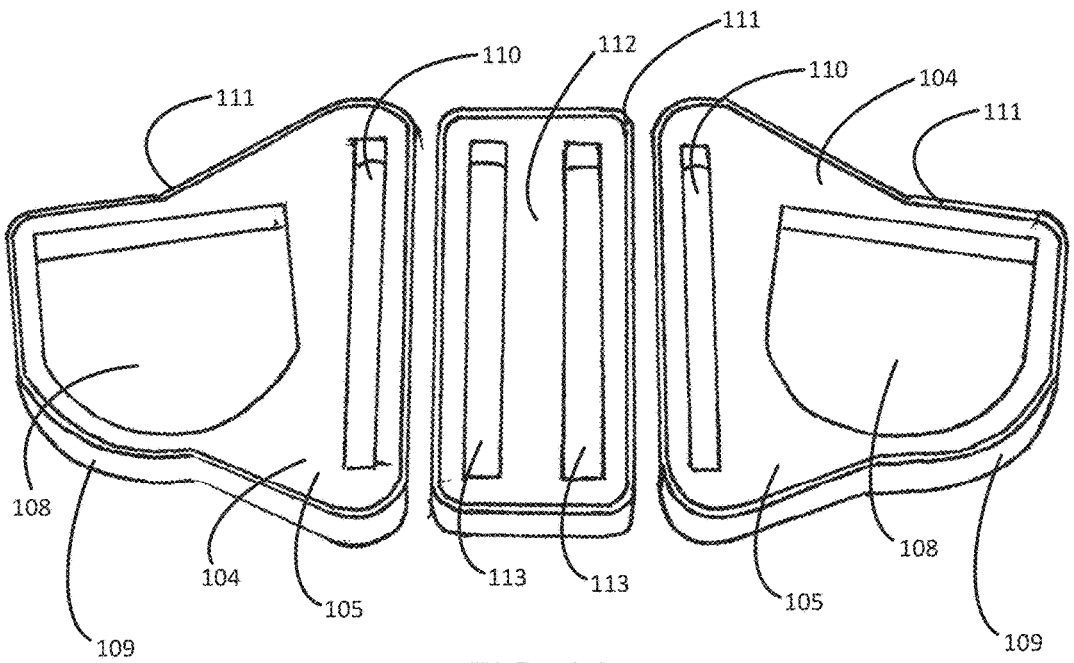
FIG. 11 depicts two adapter rings and a strap clip in accordance with an exemplary embodiment of the present invention.

As illustrated in FIGS. 7 and 10, the replacement strap 106 can include a strap clip 112 that permits the replacement strap 106 to be lengthened or shortened. It is understood, however, that other mechanisms may be used to permit the replacement strap 106 to be lengthened or shortened, such as a hook and loop fastener or a double ring closure. In some of the embodiments, a 3-D printing process is used to create the strap clip 112 from any material suitable for a 3-D printer. In a preferred embodiment using a 3-D printing process, the strap clip 112 is made from polycarbonate. It will be appreciated, however, that the strap clip 112 may be made by any other suitable manufacturing processes and materials and, in fact, may be made through the combination of one or more processes and from one or more materials. For example, the strap clip 112 may be made from any suitable plastic, metal, wood, fabric or textile or any combination thereof. As shown in FIG. 11, the strap clip 112 may have two strap apertures 113 that are sized to permit the replacement strap 106 to be passed through the strap apertures 113. In other embodiments, the strap clip 112 may instead have only one strap aperture 113. In several embodiments, the replacement strap 106 may have multiple strap clips 112. For example, the replacement strap 106 may have two strap clips 112, each strap clip 112 having only one strap aperture 113. The strap clip 112 may also include a fillet 111 at its edges. In some embodiments, the fillet 111 is between 1 mm to 2 mm in width. In several embodiments, the fillet 111 is 1.2 mm in width.

In some embodiments, the replacement strap 106 is manufactured from an elastic material that stretches in one or more directions. Suitable strap material is commonly found in the straps used on standard ski goggles and headlamps. In some embodiments, the replacement strap 106 may include a non-slip silicone strip. In several embodiments, an additional reinforcing material, such as leather or rubber, may be used to provide more structure to the replacement strap 106. The replacement strap 106 may be patterned, colored, or textured to alter the visual appearance.

Figure 8:
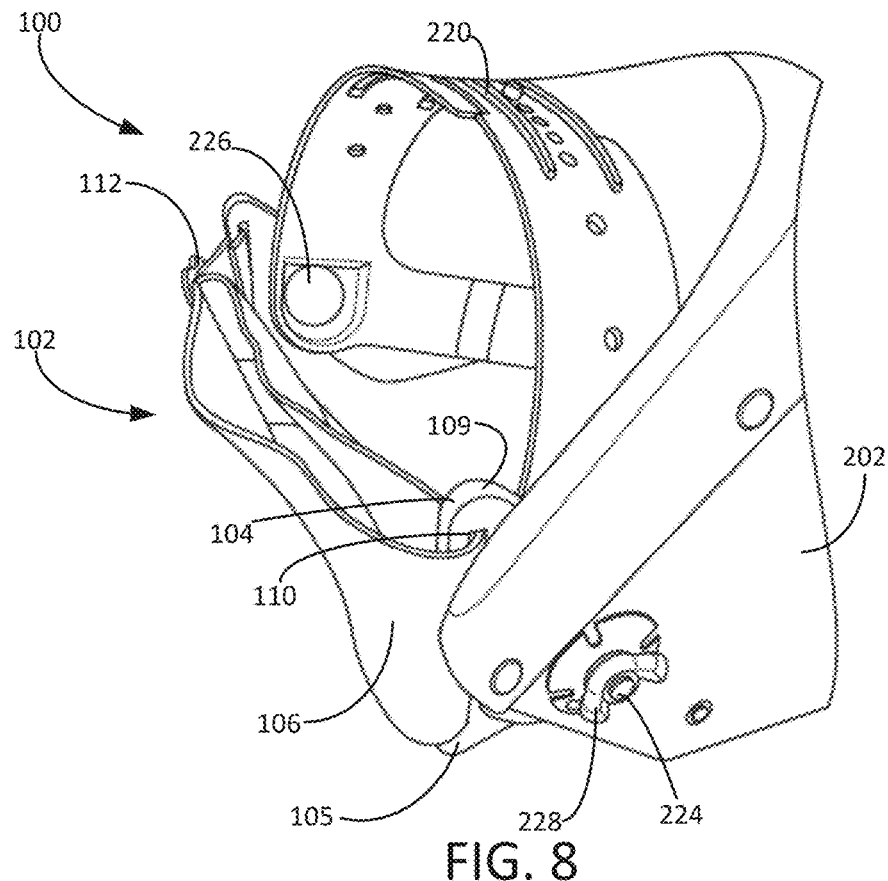
FIG. 8 provides rear perspective view of the replacement strap assembly and modified headgear assembly within the helmet.
Figure 9:
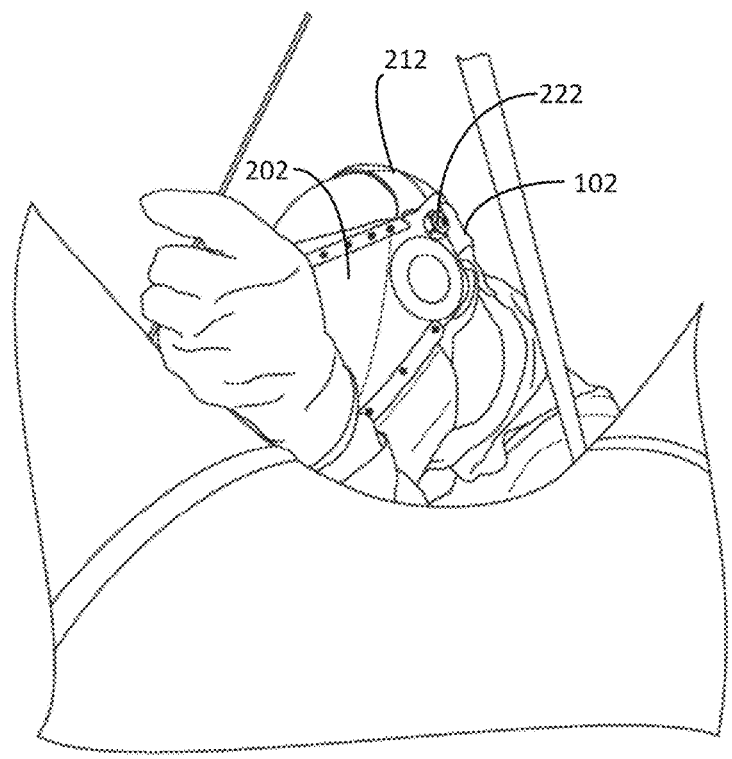
FIG. 9 depicts a welder wearing the helmet with the replacement strap assembly.

As illustrated in FIGS. 7-9, the replacement rear strap assembly 102 is attached to the modified headgear assembly 100 by removing the standard headgear assembly 206 from the helmet 200, removing the standard rear strap 210 from the standard headgear assembly 206 to provide the modified headgear assembly 100, securing the replacement rear strap assembly 102 to the modified headgear assembly 100 by placing each of the adapter rings 104 over a corresponding one of the attachment bosses 230, and then attaching the modified headgear assembly 100 to the face shield 202 with the fasteners 222. In this way, the adapter rings 104 are captured on the attachment bosses 230 between the hubs 214 and the interior of the face shield 202. The attachment bosses 230 on worn-out or older headgear may develop rough edges that make it difficult to slide hardware over the outer perimeter of the attachment bosses 230. Therefore, depending on the condition of the standard headgear assembly, it may be necessary to sand or file down these rough edges on the attachment bosses 230 before placing each of the adapter rings 104 over a corresponding one of the attachment bosses 230. It will be appreciated that the fasteners 222 may be made from any suitable material, including but not limited to metal, plastic, or wood. In most embodiments, the outer side surfaces 109 of the adapter rings 104 have approximately the same width as the side surfaces 234 of the attachment bosses 230, such that the adapter rings 104 are captured tightly between the hubs 214 and the interior of the face shield 202 during use. In other embodiments, the outer side surfaces 109 of the adapter rings 104 have a smaller width than the side surfaces 234 of the attachment bosses 230, such that the adapter rings are more loosely captured between the hubs 214 and the interior of the face shield 202. The replacement rear strap assembly 102 provides an inexpensive, durable, and comfortable modification to the standard rear strap 210 found in conventional headgear assemblies.

Although the use of the replacement rear strap assembly 102 has been illustrated in connection with the welding helmet 200, it will be understood that the replacement rear strap assembly 102 can also be used on other hats and helmets, including, but not limited to, hard hats, climbing helmets, ski helmets, bicycle helmets, and motorcycle helmets. Additionally, although the replacement rear strap assembly 102 is designed to replace the standard rear strap 210 of the standard headgear assembly 206, it will be appreciated that the replacement rear strap assembly 102 can be used in addition to, and without removing, the standard rear strap 210. In some embodiments, the standard headgear assembly 206 or modified headgear assembly 100 may not include attachment bosses 230. For those applications, the adapter rings 104 can otherwise be connected to the modified headgear assembly 100 or standard headgear assembly 206 using the fasteners 222 and a smaller adapter ring aperture 108.

It is to be understood that even though numerous characteristics and advantages of various embodiments of the present invention have been set forth in the foregoing description, together with details of the structure and functions of various embodiments of the invention, this disclosure is illustrative only, and changes may be made in detail, especially in matters of structure and arrangement of parts within the principles of the present invention to the full extent indicated by the broad general meaning of the terms in which the appended claims are expressed. It will be appreciated by those skilled in the art that the teachings of the present invention can be applied to other systems without departing from the scope and spirit of the present invention.

What is claimed is:
1. A helmet comprising:
  a headgear assembly comprising:
    a top strap;
    a front strap;
    a pair of hubs located between the top strap and the front strap; and
    a pair of attachment bosses extending from the pair of hubs, wherein each of the attachment bosses is D-shaped; and a replacement rear strap assembly attached to the headgear assembly, wherein the replacement rear strap assembly comprises:
  a pair of adapter rings, wherein each of the pair of adapter rings comprises an adapter ring aperture that is D-shaped and is sized and configured to be placed over the corresponding attachment boss; and
a replacement rear strap extending between the pair of adapter rings.

2. The helmet of claim 1, wherein the replacement rear strap comprises stretchable fabric.

* * * * *